United States Patent [19]

Jones

[11] Patent Number: 4,731,105

[45] Date of Patent: Mar. 15, 1988

[54] 1,3,4-THIADIAZOLES USEFUL AS HERBICIDES

[75] Inventor: Graham P. Jones, Sawston, England

[73] Assignee: FBC Limited, England

[21] Appl. No.: 895,921

[22] Filed: Aug. 13, 1986

[30] Foreign Application Priority Data

Aug. 17, 1985 [GB] United Kingdom ............... 8520655

[51] Int. Cl.$^4$ .................. A01N 43/82; C07D 419/12; C07D 285/12
[52] U.S. Cl. ........................................ 71/90; 544/354; 546/209; 546/165; 548/136
[58] Field of Search ............... 546/209, 165; 548/136; 71/90; 540/524; 544/354

[56] References Cited

U.S. PATENT DOCUMENTS 4,465,504 8/1984 Förster et al. ...................... 548/138

Primary Examiner—Robert T. Bond
Attorney, Agent, or Firm—Ostrolenk, Faber, Gerb & Soffen

[57] ABSTRACT

Herbicidal thiadiazolyloxyacetamides of the formula:

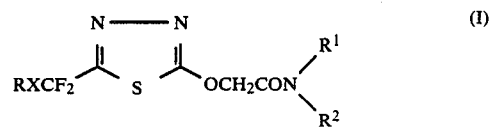

wherein: R is an optionally-substituted alkyl, cycloalkyl or aryl group; $R^1$ and $R^2$, which may be the same or different, each represent hydrogen, alkyl, cycloalkyl, alkoxy, alkenyl, aryl, aralkyl or aryloxy, any alkyl or aryl moiety thereof being optionally substituted; or $R^1$ and $R^2$, together with the nitrogen atom to which they are attached, represent a heterocyclic or benzheterocyclic group, the hetrocyclic ring of which is 5- or 6-membered, and which may be substituted by one or more alkyl groups; and X is oxygen, sulphur or $-S(O)_n-$ where n is 1 or 2, process for their preparation, and compositions containing them.

14 Claims, No Drawings

1,3,4-THIADIAZOLES USEFUL AS HERBICIDES

This invention concerns thiadiazolyloxyacetamides having herbicidal activity, processes for preparing them and compositions containing them.

In one aspect, the invention provides the thiadiazolyloxyacetamides of the formula:

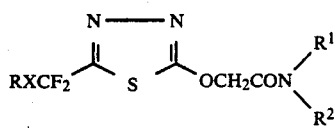

(I)

wherein: R is an optionally-substituted alkyl, cycloalkyl or aryl group; $R^1$ and $R^2$, which may be the same or different, each represent hydrogen, alkyl, cycloalkyl, alkoxy, alkenyl, aryl, aralkyl or aryloxy, any alkyl or aryl moiety thereof being optionally substituted; or $R^1$ and $R^2$, together with the nitrogen atom to which they are attached, represent a heterocyclic or benzheterocyclic group, the heterocyclic ring of which is 5- or 6-membered, and which may be substituted by one or more alkyl groups; and X is oxygen, sulphur or —S(O)$_n$— where n is 1 or 2.

When any of R, $R^1$ and $R^2$ is or contains an alkyl moiety, it is preferably of 1 to 8, particularly 1 to 6, carbon atoms. It is preferably unsubstituted, though if substituted is preferably substituted by one or more halogen atoms, especially fluorine, chlorine or bromine atoms, or by an alkoxy group of 1 to 4 carbon atoms, especially a methoxy or ethoxy group.

When any of R, $R^1$ and $R^2$ is or contains a cycloalkyl group, it is preferably of 3 to 7, and desirably of 5 or 6 carbon atoms, specific preferred cycloalkyl groups being cyclopentyl and cyclohexyl.

When any of R, $R^1$ and $R^2$ is or contains an aryl moiety, that moiety is preferably phenyl. If substituted, it is preferably substituted by one or more halogen atoms, especially chlorine or bromine atoms, or by one or more alkyl or alkoxy groups of 1 to 4 carbon atoms, especially methyl, ethyl, methoxy or ethoxy groups, or by one or more nitro groups.

When $R^1$ and/or $R^2$ represents aralkyl, it is preferably a benzyl group, which is desirably unsubstituted.

When $R^1$ and/or $R^2$ represents alkenyl, it is preferably of 2 to 6 carbon atoms, especially allyl.

When $R^1$ and $R^2$, together with the nitrogen atom to which they are attached, form or include a heterocyclic ring, that ring may if desired be further substituted, e.g. by alkyl of 1 to 4 carbon atoms, especially by methyl or ethyl, or may contain a further heteroatom, especially an oxygen atom or a further nitrogen atom. The ring may be saturated or unsaturated.

R preferably represents alkyl of 1 to 6 carbon atoms, cycloalkyl of 5 or 6 carbon atoms, alkenyl of 2 to 6 carbon atoms, phenyl, or phenyl substituted by one or more halogen atoms or alkyl groups of 1 to 4 carbon atoms.

Specific preferred groups which R may represent include methyl, ethyl, n-propyl, isopropyl, n-butyl, s-butyl, t-butyl, t-amyl, 2-methylbutyl, cyclohexyl, allyl, phenyl, 2-chlorophenyl, 4-chlorophenyl, 4-fluorophenyl, 3-methylphenyl and 2,4-dichlorophenyl.

$R^1$ and $R^2$ are preferably both other than hydrogen. When $R^1$ and $R^2$, together with the nitrogen atom to which they are attached, form a ring, it is preferably a 6-membered saturated ring, especially a piperidine ring, and particularly a piperidine ring substituted by one or more alkyl groups of 1 to 4 carbon atoms, e.g. 2-methylpiperidine, 3-methylpiperidine, 4-methylpiperidine, 2-ethylpiperidine, 2,6-dimethylpiperidine or 3,5-dimethylpiperidine. When, however, $R^1$ and $R^2$ represent independent groups, each is preferably unsubstituted alkyl of 1 to 6 carbon atoms, cycloalkyl of 5 or 6 carbon atoms, allyl, phenyl, or phenyl substituted by one or more halogen atoms or alkyl groups of 1 to 4 carbon atoms. Specific preferred such groups include methyl, ethyl, n-propyl, isopropyl, n-butyl, s-butyl, cyclohexyl, allyl, phenyl, 2-chlorophenyl, 4-chlorophenyl, 2-methylphenyl, 3-fluorophenyl, 4-methylphenyl and benzyl.

Specific preferred compounds of formula I are those of the Examples provided hereinafter, especially:
1-[5-[difluoro(isopropylthio)methyl]-1,3,4-thiadiazol-2-yloxyacetyl]-2-ethylpiperidine;
N,N-diallyl-2-[5-[difluoro(phenoxy)methyl]-1,3,4-thiadiazol-2-yloxy]acetamide;
2-[5-(ethylthio)difluoromethyl]-1,3,4-thiadiazol-2-yloxy]-N-methylacetanilide;
N,N-diallyl-2-[5-[t-butylthiodifluoromethyl]-1,3,4-thiadiazol-2-yloxy]acetamide;
2-[5-(ethylthio)difluoromethyl]-3'-fluoro-1,3,4-thiadiazol-2-yloxy]-N-methylacetanilide; and
2'-chloro-2-[5-[difluoro(phenoxy)methyl]-1,3,4-thiadiazol-2-yloxy]-N-methylacetanilide.

The compounds of formula I may be prepared by reacting a 2-halothiadiazole of the formula:

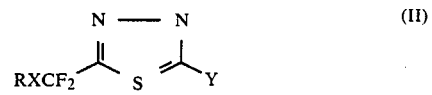

(II)

wherein R and X are as defined hereinbefore, and Y is chlorine or bromine, with a compound of the formula:

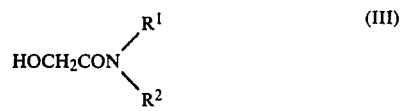

(III)

wherein $R^1$ and $R^2$ are as defined hereinbefore, in the presence of a base, to give the desired compound.

The base is preferably an inorganic base, particularly a hydroxide, alkoxide, hydride or carbonate of an alkali-metal, especially of sodium, lithium or potassium.

The compounds of formula II may be prepared from the corresponding 2-aminothiadiazoles of the formula:

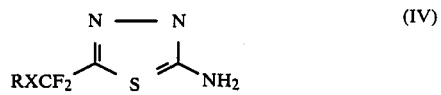

(IV)

by a conventional diazotisation technique, e.g. with sodium nitrite in the presence of a suitable solvent, e.g. acetic acid, and the appropriate hydrohalic acid HY.

In turn, the compounds of formula IV may be prepared from the known compound 2-amino-5-chlorodifluoromethylthiadiazole by reaction thereof with the appropriate alkali-metal alkoxide, aryloxide or mercaptide in a suitable solvent medium, e.g. ethanol.

The compounds of formula I where X represents S(O)$_n$ may be prepared from the corresponding compounds of formula I where X represents S by oxidation techniques known per se. For example, the compounds may be subjected to the action of an oxidising agent, for example a permanganate, chromate, peroxide or per-acid, particularly potassium permanganate, potassium chromate, hydrogen peroxide or metachloroperbenzoic acid.

The compounds of formula I have herbicidal activity. They are active in particular against grass weeds, though they do also possess significant activity against many broad-leaved species. In addition, they are comparatively safe to many crop species, particularly non-temperate crop species such as cotton, soybeans, rice and maize, but also to cereals such as wheat and barley, which may make them of use as selective herbicides.

Accordingly, in another aspect, the invention provides a method of combating weeds which comprises applying to a locus infested or liable to be infested therewith an effective amount of one or more compounds of formula I as defined hereinbefore.

Amongst the weed species combatted are barnyardgrass, crabgrass, johnsongrass, foxtails, speedwells, mayweeds, cleavers and blackgrass.

The compounds may be used either pre- or post-emergence of the crop and weed species. They are usually employed at a rate of from 0.005 to 2 kg/ha, preferably from 0.05 to 1 kg/ha, and are generally employed in the form of a composition.

In another aspect, the invention therefore provides a herbicidal composition which comprises one or more compounds of the invention in association with a suitable carrier and/or surface active agent.

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, eg a polyhalogenated alkane eg dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

If desired, the compounds of the invention may be employed in combination with a pesticide or further herbicide, especially such a compound which is useful in the location or crop concerned.

The invention is illustrated by the following Examples.

EXAMPLE 1

1-[5-[Difluoro(isopropylthio)methyl]-1,3,4-thiadiazol-2-yloxyacetyl]-2-ethylpiperidine (a)

2-Amino-5-[difluoro(isopropylthio)methyl]-1,3,4-thiadiazole

2-Amino-5-chlorodifluoromethyl-1,3,4-thiadiazole (59.6 g) was added, in one portion, to a stirred solution of 2-propanethiol (24.5 g) and sodium hydroxide (12.9 g) in ethanol (300 ml) at −40° C. The mixture was stirred at −15° C. for 2 hours and then allowed to warm to room temperature. It was then poured into water (3.5 l) and filtered to give 61.4 g of 2-amino-5-[difluoro(isopropylthio)methyl]-1,3,4-thiadiazole as a pale yellow solid m.p. 119°–121° C. (d).

(b)
2-Chloro-5-[difluoro(isopropylthio)methyl]-1,3,4-thiadiazole

2-Amino-5-[difluoro(isopropylthio)methyl]-1,3,4-thiadiazole (190 g) was dissolved in a mixture of acetic acid (880 ml) and concentrated hydrochloric acid (216.5 ml) at 60° C. A solution of sodium nitrite (171.3 g) in water (300 ml) was then added dropwise over 30 minutes at 65°–70° C. The mixture was stirred at 65° C. for 15 minutes and then allowed to cool. It was then poured onto water (3 L) and extracted with ether, the combined extracts being washed with water, dried (MgSO4) and evaporated to give an orange liquid, which was distilled under vacuum to give 150 g of 2-chloro-5-[difluoro(isopropylthio)methyl]-1,3,4-thiadiazole, bp 75°–77° C. at 0.7 mmHg.

(c)
1-[5-[Difluoro(isopropylthio)methyl]-1,3,4-thiadiazol-2-yloxyacetyl]-2-ethylpiperidine Lithium hydroxide monohydrate (9.93 g) was added portionwise to a stirred solution of 2-chloro-5-[difluoro(isopropylthio)methyl]-1,3,4-thiadiazole (36.67 g) and 1-hydroxyacetyl-2-ethylpiperidine (25.65 g) in methyl isobutyl ketone (150 ml) at 20°–24° C. over 15 minutes, and the mixture was stirred at room temperature for 2 hours, then treated with ether (200 ml) and washed with dilute hydrochloric acid. The ether solution was then dried (MgSO4) and evaporated to give an orange oil, which was purified by chromatography to give 30.2 g of 1-[5-[difluoro(isopropylthio)methyl]-1,3,4-thiadiazol-2-yloxyacetyl]-2-ethylpiperidine.

| Analysis for $C_{15}H_{23}F_2N_3O_2S_2$ | | | |
|---|---|---|---|
| | C | H | N |
| Theory | 47.47 | 6.11 | 11.07% |
| Found | 48.82 | 6.26 | 10.62% |

EXAMPLE 2

1-[5-[Difluoro(phenoxy)methyl]-1,3,4-thiadiazol-2-yloxyacetyl]-2-ethylpiperidine (a)
2-Amino-5-[difluoro(phenoxy)methyl]-1,3,4-thiadiazole 2-Amino-5-chlorodifluoromethyl-1,3,4-thiadiazole (92.7 g) was added portionwise to a stirred solution of phenol (47 g) and sodium hydroxide (20 g) in ethanol (400 ml) at 10° C. After stirring at 5° C. for 1½ hours, the solid was filtered off, washed with water and dried to give 89.6 g of 2-amino-5-[difluoro(phenoxy)-methyl]-1,3,4-thiadiazole, m.p. 149°–151° C.

(b)
2-Bromo-5-[difluoro(phenoxy)methyl]-1,3,4-thiadiazole

A solution of sodium nitrite (33 g) in water (60 ml) was added dropwise to a stirred solution of 2-amino-5-[difluoro(phenoxy)methyl]-1,3,4-thiadiazole (39.5 g) in acetic acid (175 ml) and 48% hydrobromic acid (40 ml) at 60° C. over 30 minutes. The mixture was stirred at 70° C. for 15 minutes and allowed to cool.

The mixture was then poured into water (2 l) and the product was extracted into ether, and the combined extracts were washed with water and dried (MgSO4).

The ether was then evaporated to give 40 g of 2-bromo-5-[difluoro(phenoxy)methyl]-1,3,4-thiadiazole as an orange oil.

(c)
1-[5-[Difluoro(phenoxy)methyl]-1,3,4-thiadiazol-2-yloxyacetyl]-2-ethylpiperidine 2-Bromo-5-[difluoro(phenoxy)methyl]-1,3,4-thiadiazole (6.14 g) was added portionwise to a stirred solution of 1-hydroxyacetyl-2-ethylpiperidine (3.44 g) and potassium t-butoxide (2.25 g) in t-butanol (15 ml) at 25° C. over 5 minutes, and the mixture was stirred at 25° C. for 2 hours. It was then treated with ether (200 ml) and washed with 2N hydrochloric acid and saturated sodium chloride solution.

The ether solution was dried (MgSO4) and evaporated to give an orange oil, and purified by chromatography to give 2.8 g of 1-[5-[difluoro(phenoxy)-methyl]-1,3,4-thiadiazol-2-yloxyacetyl]-2-ethylpiperidine as a yellow oil.

| Analysis for $C_{18}H_{21}F_2N_3O_3S$ | | | |
|---|---|---|---|
| | C | H | N |
| Theory | 54.39 | 5.33 | 10.57% |
| Found | 53.93 | 5.25 | 10.28% |

EXAMPLES 3–150

The following compounds of formula I were prepared by processes analogous to those of Examples 1 and 2:

| No | R | X | R¹ | R² | M. Pt (°C.) |
|---|---|---|---|---|---|
| 3 | phenyl | O | phenyl | ethyl | 102–103 |
| 4 | phenyl | O | ethyl | ethyl | oil |
| 5 | phenyl | O | phenyl | methyl | 82–83 |
| 6 | phenyl | O | allyl | allyl | oil |
| 7 | ethyl | S | phenyl | methyl | 74–75 |
| 8 | ethyl | S | 1-ethylpentane-1,5-diyl | | oil |
| 9 | isopropyl | S | 2,4-dimethylpentane-1,5-diyl | | oil |
| 10 | isopropyl | S | allyl | allyl | oil |
| 11 | isopropyl | S | 2-methylpentane-1,5-diyl | | oil |
| 12 | isopropyl | S | 1-methylpentane-1,5-diyl | | oil |
| 13 | isopropyl | S | ethyl | ethyl | oil |
| 14 | isopropyl | S | n-propyl | n-propyl | oil |
| 15 | isopropyl | S | methyl | cyclohexyl | oil |
| 16 | t-butyl | S | allyl | allyl | oil |
| 17 | t-butyl | S | 1-ethylpentane-1,5-diyl | | oil |
| 18 | isopropyl | S | 3-methylpentane-1,5-diyl | | oil |
| 19 | isopropyl | S | n-butyl | methyl | oil |
| 20 | t-butyl | S | 1-methylpentane-1,5-diyl | | oil |
| 21 | n-butyl | S | 1-ethylpentane-1,5-diyl | | oil |
| 22 | n-butyl | S | allyl | allyl | oil |
| 23 | t-butyl | S | ethyl | ethyl | oil |
| 24 | n-butyl | S | 1-methylpentane-1,5-diyl | | oil |
| 25 | isopropyl | S | 1,5-dimethylpentane-1,5-diyl | | 40–44 |
| 26 | n-butyl | S | n-propyl | n-propyl | oil |
| 27 | ethyl | S | allyl | allyl | oil |
| 28 | ethyl | S | n-propyl | n-propyl | oil |
| 29 | isopropyl | S | pentane-1,5-diyl | | oil |
| 30 | phenyl | O | n-propyl | n-propyl | oil |
| 31 | isopropyl | S | methyl | phenyl | 99.5–101 |
| 32 | t-butyl | S | methyl | phenyl | 58–60 |
| 33 | isopropyl | S | hexane-1,6-diyl | | oil |
| 34 | ethyl | S | methyl | n-butyl | oil |
| 35 | ethyl | S | 1-methylpentane-1,5-diyl | | oil |
| 36 | ethyl | S | ethyl | ethyl | oil |
| 37 | phenyl | O | pentane-1,5-diyl | | 96–98 |
| 38 | phenyl | O | 1-methylpentane-1,5-diyl | | 68–70 |
| 39 | phenyl | O | hexane-1,6-diyl | | 50–52.5 |

-continued

| No | R | X | R¹ | R² | M. Pt (°C.) |
|---|---|---|---|---|---|
| 40 | phenyl | O | allyl | n-propyl | oil |
| 41 | 2,4-dichlorophenyl | O | allyl | allyl | oil |
| 42 | 2,4-dichlorophenyl | O | 1-ethylpentane-1,5-diyl | | oil |
| 43 | isopropyl | S | phenyl | ethyl | 92–93 |
| 44 | n-butyl | S | phenyl | methyl | 38–40 |
| 45 | phenyl | O | benzyl | methyl | oil |
| 46 | 4-chlorophenyl | O | 1-ethylpentane-1,5-diyl | | oil |
| 47 | phenyl | O | isopropyl | isopropyl | 82–83.5 |
| 48 | isopropyl | S | isopropyl | isopropyl | 70–72 |
| 49 | 4-chlorophenyl | O | allyl | allyl | oil |
| 50 | 2-chlorophenyl | O | 1-ethylpentane-1,5-diyl | | oil |
| 51 | 3-methylphenyl | O | 1-ethylpentane-1,5-diyl | | oil |
| 52 | 2-chlorophenyl | O | allyl | allyl | oil |
| 53 | isobutyl | S | phenyl | methyl | 60–61 |
| 54 | isobutyl | S | 1-ethylpentane-1,5-diyl | | 56–57 |
| 55 | isobutyl | S | 1-methylpentane-1,5-diyl | | oil |
| 56 | s-butyl | S | phenyl | methyl | 63–64 |
| 57 | s-butyl | S | n-butyl | methyl | oil |
| 58 | n-butyl | S | n-butyl | methyl | oil |
| 59 | s-butyl | S | allyl | allyl | oil |
| 60 | phenyl | O | allyl | isopropyl | oil |
| 61 | isopropyl | S | isopropyl | allyl | oil |
| 62 | s-butyl | S | 1-ethylpentane-1,5-diyl | | oil |
| 63 | 4-fluorophenyl | O | n-propyl | n-propyl | oil |
| 64 | 4-fluorophenyl | O | n-propyl | allyl | oil |
| 65 | 4-fluorophenyl | O | 1-ethylpentane-1,5-diyl | | oil |
| 66 | 4-fluorophenyl | O | allyl | allyl | oil |
| 67 | 3-methylphenyl | O | allyl | allyl | oil |
| 68 | isobutyl | S | n-propyl | n-propyl | oil |
| 69 | ethyl | S | methyl | 4-methylphenyl | oil |
| 70 | t-butyl | S | methyl | 4-methylphenyl | oil |
| 71 | isopropyl | S | methyl | 3-methylphenyl | oil |
| 72 | n-butyl | S | methyl | 3-methylphenyl | oil |
| 73 | s-butyl | S | methyl | 3-methylphenyl | oil |
| 74 | phenyl | O | methyl | 4-methylphenyl | 99–100 |
| 75 | ethyl | S | hexane-1,6-diyl | | oil |
| 76 | ethyl | S | methyl | 2-chlorophenyl | 77–78 |
| 77 | ethyl | S | methyl | 2-methylphenyl | 99–100 |
| 78 | isopropyl | S | allyl | n-propyl | oil |
| 79 | isobutyl | S | allyl | allyl | oil |
| 80 | 2,4-dichlorophenyl | O | allyl | n-propyl | oil |
| 81 | cyclohexyl | S | phenyl | methyl | 90–91 |
| 82 | phenyl | O | methyl | 2-chlorophenyl | oil |
| 83 | phenyl | O | methyl | 2-methylphenyl | oil |
| 84 | ethyl | S | methyl | 4-chlorophenyl | 85–86 |
| 85 | t-butyl | S | methyl | 2-methylphenyl | 99–100 |
| 86 | t-butyl | S | methyl | 2-chlorophenyl | 88–89 |
| 87 | t-butyl | S | n-propyl | n-propyl | oil |
| 88 | t-butyl | S | allyl | n-propyl | oil |
| 89 | cyclohexyl | S | 1-ethylpentane-1,5-diyl | | 76–77 |
| 90 | cyclohexyl | S | allyl | allyl | oil |
| 91 | cyclohexyl | S | 1-methyl-pentane-1,5-diyl | | oil |
| 92 | t-butyl | S | methyl | 4-chlorophenyl | 78–79 |
| 93 | t-butyl | S | hexane-1,6-diyl | | 49–50 |
| 94 | phenyl | O | methyl | 4-chlorophenyl | 110–111 |
| 95 | t-butyl | S | isopropyl | allyl | oil |
| 96 | isopropyl | S | methyl | 4-chlorophenyl | oil |
| 97 | ethyl | S | methyl | 4-methylphenyl | 46–47 |
| 98 | n-propyl | S | 1-ethylpentane-1,5-diyl | | oil |
| 99 | n-propyl | S | allyl | allyl | oil |
| 100 | t-amyl | S | phenyl | methyl | 52–54 |
| 101 | t-butyl | S | methyl | 3-chlorophenyl | 67–68 |
| 102 | ethyl | S | methyl | 3-chlorophenyl | oil |
| 103 | n-propyl | S | phenyl | methyl | 67–68 |
| 104 | n-propyl | S | allyl | isopropyl | oil |
| 105 | n-propyl | S | 1-methylpentane-1,5-diyl | | oil |
| 106 | t-amyl | S | allyl | allyl | oil |
| 107 | t-amyl | S | allyl | n-propyl | oil |
| 108 | t-butyl | S | 2-methylpentane-1,5-diyl | | 61–63 |
| 109 | phenyl | O | methyl | 3-chlorophenyl | 48–52 |
| 110 | t-butyl | S | s-butyl | allyl | oil |
| 111 | phenyl | O | s-butyl | allyl | oil |
| 112 | ethyl | S | s-butyl | allyl | oil |
| 113 | cyclohexyl | S | hexane-1,6-diyl | | 71–72 |
| 114 | t-amyl | S | 1-ethylpentane-1,5-diyl | | oil |
| 115 | t-amyl | S | isopropyl | allyl | oil |
| 116 | t-amyl | S | n-propyl | n-propyl | oil |
| 117 | 2-chlorophenyl | O | pentane-1,5-diyl | | 88–90 |
| 118 | 2-chlorophenyl | O | n-propyl | n-propyl | oil |
| 119 | t-amyl | S | 3-methylpentane-1,5-diyl | | oil |
| 120 | n-propyl | S | n-propyl | allyl | oil |
| 121 | phenyl | O | isobutyl | n-butyl | oil |
| 122 | ethyl | S | isobutyl | n-butyl | oil |
| 123 | phenyl | O | isopropyl | n-propyl | oil |
| 124 | t-amyl | S | pentane-1,5-diyl | | oil |
| 125 | t-amyl | S | 1-methylpentane-1,5-diyl | | oil |
| 126 | n-butyl | S | n-propyl | isopropyl | oil |
| 127 | t-amyl | S | n-propyl | isopropyl | oil |
| 128 | isobutyl | S | n-propyl | isopropyl | oil |
| 129 | t-butyl | S | n-propyl | isopropyl | oil |
| 130 | ethyl | S | isopropyl | n-propyl | oil |
| 131 | t-amyl | S | 2-methylpentane-1,5-diyl | | oil |
| 132 | 2-methylbutyl | S | phenyl | methyl | oil |
| 133 | 2-methylbutyl | S | 1-methylpentane-1,5-diyl | | oil |
| 134 | ethyl | S | methyl | 4-fluorophenyl | 80–84 |
| 135 | phenyl | O | methyl | 4-fluorophenyl | 90–93 |
| 136 | t-butyl | S | methyl | 4-fluorophenyl | 72–74 |
| 137 | ethyl | S | methyl | 3-fluorophenyl | 69–72 |
| 138 | phenyl | O | methyl | 2-fluorophenyl | 62–64 |
| 139 | 2-fluorophenyl | O | allyl | allyl | oil |
| 140 | 3-fluorophenyl | O | allyl | allyl | oil |
| 141 | 3-fluorophenyl | O | 1-methylpentane-1,5-diyl | | 60–62 |
| 142 | 3-methylbutyl | S | methyl | phenyl | 75–77 |
| 143 | 3-methylbutyl | S | allyl | allyl | oil |
| 144 | methyl | S | methyl | 3-methylphenyl | oil |
| 145 | methyl | S | hexane-1,6-diyl | | 44–46 |
| 146 | methyl | S | n-propyl | n-propyl | oil |
| 147 | methyl | S | methyl | 2-methylphenyl | 82–84 |
| 148 | methyl | S | methyl | phenyl | 74–80 |
| 149 | 2-fluorophenyl | O | allyl | n-propyl | oil |
| 150 | 2-fluorophenyl | O | 1-methylpentane-1,5-diyl | | 68–72 |

EXAMPLE 151

2-[5-(ethylsulphonyldifluoromethyl)-1,3,4-thiadiazol-2-yloxy]-N-methyl-N-phenylacetamide A solution of potassium permanganate (3.16 g) in water (75 ml) was added dropwise to a stirred solution of the product of Example 7 (5.36 g) in acetic acid (20 ml) at 25°–30° C. The mixture was stirred at room temperature for 5 minutes and was poured into water (100 ml). Sodium metabisulphite was added portionwise until the mixture was colourless. The resulting white solid was filtered off, washed with water and crystallised from propan-2-ol to give 2.8 g of desired product as a white solid, mp 103°–104° C.

EXAMPLE 152–154

The following compounds were prepared by methods analogous to that of Example 151:

| No | R | X | R¹ | R² | M. Pt (°C.) |
|---|---|---|---|---|---|
| 152 | 2-methylbutyl | SO₂ | 1-methylpentane-1,5-diyl | | oil |
| 153 | ethyl | SO₂ | hexane-1,6-diyl | | 79–80 |
| 154 | methyl | SO₂ | hexane-1,6-diyl | | 87–88 |

EXAMPLE 155–156

The following compounds were prepared by methods analogous to that of Example 1:
155. 1-[5-(isopropylthiodifluoromethyl)-1,3,4-thiadiazol-2-yloxyacetyl]-1,2,3,4-tetrahydroquinoline, oil.
156. 4-[5-(t-butylthiodifluoromethyl)-1,3,4-thiadiazol-2-yloxyacetyl]-3,4-dihydroquinoxalin-2-(1H)-one, oil.

EXAMPLE A

Seeds of the plant species listed below were sown in 750 mm diameter plastic pots containing sterilised sandy loam. They were watered and then sprayed with the compounds of the Examples listed below formulated as a solution in 3:1 by volume of acetone:water containing the wetting agent polyoxyethylene (20 mols) monolaurate solution (0.25 g per liter).

The concentration of each test compound and volume of application were calculated to give a rate of application of the compound of 0.25 kg/ha in 200 liters per hectare. After 22 days growth in the glasshouse (minimum temperature 15° C., maximum 25° C.) the plants were visually assessed for any herbicidal response. All differences from an untreated control were scored.

In the table below, the following letters are used to denote the plant species:
a—*Gossypium hirsutum* (cotton)
b—*Glycine max* (soybeans)
c—*Helianthus annuus* (sunflower)
d—*Zea mays* (maize)
e—*Oryza sativa* (rice)
f—*Alopecurus myosuroides* (blackgrass)
g—*Echinochloa crus-galli* (barnyardgrass)
h—*Sorghum halepense* (Johnsongrass)
i—*Setaria faberii* (giant foxtail)
j—*Digitaria sanguinalis* (crabgrass)
k—*Panicum capillare* (witchgrass)
l—*Setaria viridis* (green foxtail)

Percentage control was as follows:

| Ex No | a | b | c | d | e | f | g | h | i | j | k | l |
|---|---|---|---|---|---|---|---|---|---|---|---|---|
| 1 | 5 | 0 | 5 | 10 | 15 | 95 | 99 | 99 | 95 | 95 | 95 | 97 |
| 2 | 0 | 0 | 0 | 5 | 10 | 98 | 99 | 85 | 90 | 98 | 98 | 80 |
| 4 | 5 | 0 | 0 | 20 | 15 | 90 | 98 | 97 | 93 | 80 | 99 | 85 |
| 5 | 5 | 0 | 0 | 15 | 20 | 70 | 99 | 90 | 85 | 95 | 90 | 95 |
| 6 | 20 | 0 | 10 | 10 | 0 | 85 | 99 | 97 | 95 | 100 | 99 | 95 |
| 7 | 15 | 0 | 0 | 5 | 5 | 65 | 95 | 90 | 85 | 95 | 97 | 95 |
| 8 | 0 | 0 | 0 | 0 | 0 | 60 | 93 | 75 | 75 | 95 | 97 | 80 |
| 10 | 5 | 0 | 0 | 5 | 0 | 75 | 90 | 90 | 90 | 98 | 95 | 97 |
| 11 | 0 | 0 | 5 | 0 | 0 | 75 | 90 | 90 | 65 | 60 | 92 | 60 |
| 12 | 15 | 0 | 0 | 20 | 0 | 97 | 95 | 85 | 85 | 98 | 97 | 97 |
| 14 | 5 | 5 | 0 | 10 | 0 | 75 | 99 | 99 | 90 | 85 | 98 | 85 |
| 16 | 0 | 0 | 0 | 0 | 0 | 100 | 98 | 95 | 92 | 95 | 100 | 95 |
| 17 | 10 | 0 | 0 | 40 | 0 | 90 | 97 | 85 | 97 | 99 | 99 | 97 |
| 18 | 10 | 0 | 0 | 20 | 0 | 97 | 80 | 90 | 85 | 85 | 95 | 98 |
| 20 | 5 | 0 | 0 | 0 | 0 | 100 | 99 | 95 | 90 | 98 | 100 | 98 |
| 27 | 0 | 0 | 0 | 0 | 0 | 70 | 35 | 60 | 0 | 85 | 85 | 80 |
| 32 | 0 | 0 | 0 | 15 | 5 | 80 | 95 | 95 | 99 | 97 | 99 | 99 |
| 37 | 10 | 0 | 0 | 5 | 0 | 50 | 70 | 65 | 60 | 85 | 80 | 65 |
| 38 | 10 | 0 | 0 | 0 | 5 | 90 | 97 | 95 | 93 | 99 | 100 | 85 |
| 40 | 0 | 0 | 0 | 0 | 10 | 85 | 98 | 98 | 90 | 99 | 99 | 98 |
| 53 | 15 | 0 | 0 | 0 | 0 | 75 | 93 | 95 | 90 | 95 | 93 | 99 |
| 54 | 5 | 0 | 0 | 15 | 0 | 35 | 80 | 85 | 85 | 95 | 97 | 80 |
| 56 | 5 | 0 | 0 | 5 | 0 | 70 | 97 | 80 | 85 | 93 | 97 | 95 |
| 59 | 5 | 0 | 0 | 10 | 0 | 85 | 90 | 95 | 85 | 99 | 97 | 95 |
| 60 | 0 | 0 | 0 | 0 | 0 | 90 | 99 | 100 | 90 | 85 | 97 | 75 |
| 61 | 0 | 0 | 10 | 10 | 15 | 98 | 97 | 95 | 90 | 95 | 98 | 97 |
| 62 | 0 | 0 | 10 | 0 | 15 | 90 | 97 | 85 | 95 | 97 | 95 | 90 |

EXAMPLE B

An emulsifiable concentrate was prepared by dissolving 500 g of the compound of Example 1, 50 g of Arylan CA (calcium dodecylbenzene sulphonate) and 50 g of Ethylan C40AH (condensation product of ethylene oxide and castor oil) in sufficient xylene to produce 1 liter. Analogous formulations were also prepared containing 5 g, 50 g, 200 g and 750 g of the compounds of Examples 1–156.

I claim:

1. A thiadiazolyloxyacetamide of the formula:

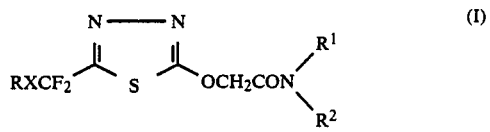

wherein: R is alkyl of 1 to 8 carbon atoms, cycloalkyl of 3 to 7 carbon atoms, or phenyl which is unsubstituted or substituted by one or two halogen atoms or alkyl or alkoxy groups of 1 to 4 carbon atoms; $R^1$ and $R^2$, which may be the same or different, each represent hydrogen, alkyl of 1 to 8 carbon atoms, cycloalkyl of 3 to 7 carbon atoms, alkenyl of 2 to 6 carbon atoms, benzyl, or phenyl which is unsubstituted or substituted by one or two halogen atoms, nitro groups, or alkyl or alkoxy groups of 1 to 4 carbon atoms; or $R^1$ and $R^2$ are linked to form a 5- or 6-membered saturated carbon chain and which is unsubstituted or substituted by one or two alkyl groups of 1 to 4 carbon atoms; and X is oxygen, sulphur, or —S(O)$_n$— where n is 1 or 2.

2. The thiadiazolyloxyacetamide according to claim 1 wherein R is methyl, ethyl, propyl, butyl, methylbutyl, cyclohexyl, phenyl, chlorophenyl, dichlorophenyl, fluorophenyl or methylphenyl; $R^1$ and $R^2$ are individually selected from the group consisting of methyl, ethyl, propyl, butyl, allyl, phenyl, phenyl substituted by chloro, methyl or fluoro, and benzyl, or $R^1$ and $R^2$ together with the nitrogen atom to which they are attached form a 6-membered saturated ring; and X is oxygen or sulphur.

3. The thiadiazolyloxyacetamide according to claim 1 wherein R represents alkyl of 1 to 6 carbon atoms, cycloalkyl of 5 or 6 carbon atoms, phenyl, or phenyl substituted by one or two halogen atom or alkyl group of 1 to 4 carbon atoms.

4. The thiadiazolyloxyacetamide according to claim 1 or claim 2 wherein $R^1$ represents alkyl of 1 to 6 carbon atoms, cycloalkyl of 5 or 6 carbon atoms, allyl, phenyl, or phenyl substituted by one or two halogen atom or alkyl group of 1 to 4 carbon atoms.

5. The thiadiazolyloxyacetamide according to claim 1 or 3 wherein $R^2$ represents alkyl of 1 to 6 carbon atoms, cycloalkyl of 5 or 6 carbon atoms, allyl, phenyl, or phenyl substituted by one or two halogen atoms or alkyl groups of 1 to 4 carbon atoms.

6. The thiadiazolyloxyacetamide according to claim 1 or claim 2 wherein $R^1$ and $R^2$ together with the nitrogen atom to which they are attached form a piperidine ring unsubstituted or substituted by at least one alkyl group of 1 to 4 carbon atoms.

7. A thiadiazolyloxyacetamide selected from:
1-[5-[difluoro(isopropylthio)methyl]-1,3,4-thiadiazol-2-yloxyacetyl]-2-ethylpiperidine;
N,N-diallyl-2-[5-[difluoro(phenoxy)methyl]-1,3,4-thiadiazol-2-yloxy]acetamide;
2-[5-(ethylthio)difluoromethyl]-1,3,4-thiadiazol-2-yloxy]-N-methylacetanilide;
N,N-diallyl-2-[5-[t-butylthiodifluoromethyl]-1,3,4-thiadiazol-2-yloxy]acetamide;
2-[5-(ethylthio)difluoromethyl]-3'-fluoro-1,3,4-thiadiazol-2-yloxy]-N-methylacetanilide; and 2'-chloro-2-[5-[difluoro(phenoxy)methyl]-1,3,4-thiadiazol-2-yloxy]-N-methylacetanilide.

8. The thiadiazolyloxyacetamide according to claim 4 wherein $R^2$ represents alkyl of 1 to 6 carbon atoms, cycloalkyl of 5 or 6 carbon atoms, allyl, phenyl, or phenyl substituted by one or two halogen atom or alkyl group of 1 to 4 carbon atoms.

9. A herbicidal composition which comprises from 0.1 to 99% by weight of at least one or more compound according to claim 1 or claim 2 in association with a suitable carrier and/or surface active agent.

10. A method of combating weeds which comprises applying to a locus infested or liable to be infested therewith an effective amount of at least one compound according to of claim 1 or claim 2.

11. A herbicidal composition which comprises from 0.1 to 99% by weight of at least one compound according to claim 4 in association with a suitable carrier and/or surface active agent.

12. A herbicidal composition which comprises from 0.1 to 99% by weight of at least one or more compound according to claim 6 in association with a suitable carrier and/or surface active agent.

13. A method of combatting weeds which comprises applying to a locus infested or liable to be infested therewith an effective amount of at least one compound according to any of claim 4.

14. A method of combatting weeds which comprises applying to a locus infested or liable to be infested therewith an effective amount of at least one compound according to claim 6.

* * * * *